(12) United States Patent
Maiefski et al.

(10) Patent No.: US 6,528,324 B1
(45) Date of Patent: Mar. 4, 2003

(54) APPARATUS FOR PRE-DETERMINED MASS SORTING OF POSITIONAL-ENCODED SOLID PHASE SYNTHESIS SUPPORTS

(75) Inventors: Romaine R. Maiefski, Oceanside, CA (US); Edmund J. Moran, San Francisco, CA (US); Thomas J. Baiga, Oceanside, CA (US)

(73) Assignee: Ontogen Corporation, Carlsbad, CA (US)

( * ) Notice: Subject to any disclaimer, the term of this patent is extended or adjusted under 35 U.S.C. 154(b) by 0 days.

(21) Appl. No.: 09/500,249

(22) Filed: Feb. 8, 2000

Related U.S. Application Data

(63) Continuation-in-part of application No. 08/822,210, filed on Mar. 21, 1997, now abandoned
(60) Provisional application No. 60/013,897, filed on Mar. 22, 1996.

(51) Int. Cl.⁷ .................. G01N 33/543; C12M 1/00; A61K 38/00
(52) U.S. Cl. ............... 436/518; 435/289.1; 435/294.1; 435/DIG. 46; 435/DIG. 49; 435/DIG. 43; 536/23.1; 536/25.1; 530/333; 530/339
(58) Field of Search ................ 436/518, 536; 536/23.1, 25.3; 530/333, 339; 435/DIG. 1, DIG. 34, DIG. 35, DIG. 37, DIG. 38, DIG. 40, DIG. 43, DIG. 46, DIG. 49, 6, 283.1, 289.1, 292.1, 294.1

(56) References Cited

U.S. PATENT DOCUMENTS

| | | |
|---|---|---|
| 4,631,211 A | 12/1986 | Houghton |
| 5,288,514 A | 2/1994 | Ellman et al. |
| 5,324,483 A | 6/1994 | Cody et al. |
| 5,565,324 A | 10/1996 | Still et al. |
| 5,792,431 A | 8/1998 | Moore et al. |
| 5,885,837 A | 3/1999 | Winkler et al. |

FOREIGN PATENT DOCUMENTS

| | | | | |
|---|---|---|---|---|
| WO | WO 94/05394 | 3/1994 | ......... | G01N/33/552 |
| WO | WO 00/40331 | 7/2000 | ............ | B01J/19/00 |
| WO | WO 00/49382 | 8/2000 | ............ | G01N/1/28 |

OTHER PUBLICATIONS

Frank Ronald., Bioorganic & Medincinal Chemstriy Letters, vol. 3, No. 3, pp 425–430, 1993.*

Geyson H. Mario; *Use of peptide synthesis to probe viral antigens for epitopes to a resolution of a single amino acid*; Proc. Natl. Acad. Sci. (1984) 3998–4002:81.

Fodor, Stephen P. et al; *Light–Directed, Spatially Adressable Parallel Chemical Synthesis*; Science; (1991) 767–773:251.

Gallop, Mark A. et al; *Applications of Combinatorial Technologies to Drug Discovery. I. Background and Peptide Combinatorial Libraries*; Journal of Medicinal Chemistry, (1994); 1233–1251:37(9).

Gallop et al. "Applications of Combinatorial Technologies to Drug Discovery". *J. Medicinal Chem.* 37(9):1233–1251 (1994).

Birnbaum and Mosbach. "Peptide Screening". *Current Op. in Biotechnology* 3(1):49–54 (1992).

\* cited by examiner

*Primary Examiner*—Padmashri Ponnaluri
(74) *Attorney, Agent, or Firm*—Freling E. Baker; Jay M. Brown

(57) ABSTRACT

A system for producing a library of oligomer comprising at least two monomers in a positionally determined array comprise a plurality of synthesis supports, a first plurality of support carriers wherein each carrier has a uniform array of distinct support holding positions for the synthesis supports; means for contacting each array of synthesis supports with a different monomer to provide a first chemical transformation of the synthesis supports; a second plurality of support carriers wherein each carrier has a uniform array of distinct support holding positions for receiving the chemically transformed synthesis supports contained in the first plurality of support carriers; transfer apparatus for transferring a selected row or column of synthesis supports from each of the first plurality of carriers to each of the second plurality of carriers to enable the supports in the second to undergo at least a second chemical transformation; and whereby each support position in each carrier identifies the chemical compound thereon.

10 Claims, 14 Drawing Sheets

(24X24 ARRAY)

APPARATUS FOR PRE-DETERMINED MASS SORTING OF POSITIONAL-ENCODED SOLID PHASE SYNTHESIS SUPPORTS

REFERENCE TO RELATED APPLICATIONS

This Application is a continuation-in-part of application Ser. No. 08/822,210, filed Mar. 21, 1997, now abandoned which claims the benefit of the filing date of the Provisional Application Serial No. 60/013,897, filed Mar. 22, 1996.

FIELD OF THE INVENTION

The present invention relates to apparatus and methods for carrying out multiple different operations on multiple articles and establishing the operations on each article by its position in the array.

The present invention relates to apparatus and method useful in creating combinatorial chemistry libraries. More particularly, the present invention relates to apparatus and methods for synthesizing spatially-dispersed positionally encoded combinatorial chemistry libraries of oligomer whereby the synthesis is carried out on a plurality of solid supports which in turn are distributed in the form of a series of arrays. The position of each solid support in each array determines the exact identity of the oligomer.

BACKGROUND OF THE INVENTION

The screening of chemical libraries to identify compounds which have novel pharmacological and material science properties is a common practice. These chemical libraries may be a collection of structurally related oligopeptides, oligonucleotides, small or large molecular weight organic or inorganic molecules. Those practiced in the art of combinatorial chemistry can accomplish the synthesis of combinatorial chemical libraries using two general methods. These methods are known to those skilled in the art as "spatially-addressable" methods and "split-pool" methods. It is common to practice these methods using solid support chemical synthesis techniques as discussed by Gordon, et al.

A common feature to the spatially-addressable combinatorial library methods is that a unique combination of monomers is reacted to form a single oligomer or compound or, alternately, set of oligomer or compounds at a predefined unique physical location or address in the synthesis process. An example of the spatially-addressable method is provided by Geysen et al. and involves the generation of peptide libraries on an array of immobilized polymeric pins (a solid support) that fit the dimensions of a 96-well microtiter plate. A two-dimensional matrix of combinations is generated in each microtiter plate experiment, where n×m unique oligomer or compounds are produced for a combination of n+rn parallel monomer addition steps. The structure of each of the individual library members is determined by analyzing the pin location and the monomers employed at that address during the sequence of reaction steps in the synthesis.

An advantage of this method is that individual oligomer or compound products can be released from the polymeric pin surface in a spatially-addressable manner to allow isolation and screening of each discrete member of the library. Another advantage of this method is that the number of solid supports required is equal to, i.e. no larger than, the number of library members to be synthesized. Thus, relatively large quantities, i.e. micromolar quantities, of individual library members are synthesized in a practical manner using this method.

Related to the Geysen pin method are the parallel synthesis methods which use a reaction vessel system such as that practiced by Cody, et al. This is the practice of distributing a quantity of solid supports, such as chemically-derivatized polymeric resin beads (namely those of the composition polystyrene, polystyrene grafted with polyethylene glycol, or polyacrylimide, etc.) in a two dimensional matrix of n×m individual reaction vessels allowing the parallel addition of a set of n×m reactive monomers to produce a set of n×m oligomer; or compounds. This spatially-addressable method has advantages similar to that of Geysen, et al. Thus, individual oligomer or compound products can be released from the solid support in a spatially-addressable manner to allow isolation and screening of each discrete member of the library. Additionally, the number of solid supports required is equal to, i.e. no larger than, the number of library members to be synthesized. Thus, relatively large quantities, i.e. micromolar to millimolar quantities, of individual library members also are synthesized in a practical manner using this method.

Another example of a spatially-addressable method is the photo lithographic method for synthesizing a collection oligomer or compounds on the chemically-derivatized surface of a chip (a solid support) provided by Fodor et al. A variety of masking strategies can be employed to selectively remove photochemically-labile protecting groups thus revealing reactive functional groups at defined spatial locations on the chip. The functional groups are reacted with a monomer by exposing the chip surface to appropriate reagents. The sequential masking and reaction steps are recorded, thus producing a pre-defined record of discrete oligomer or compounds at known spatial addresses in an experiment. An advantage of this method is that binary masking strategies can be employed to produce a unique oligomer or compounds for n masking and monomer addition cycles. Two important disadvantages of this method are that a) relatively minute quantities are produced on the surface of the chip and; b) release and isolation of individual library members is not technically feasible.

Split-pool combinatorial library methods differ from spatially addressable methods in that the physical location of each unique oligomer or compound is not discrete. Instead, pools of library members are manipulated throughout the experiment. There are two major categories of split-pool methods currently in practice. These are: 1) deconvolution method S7 pioneered by Furka et al. and Houghten, et al. and 2) encoded methods by Gallop et al., Still, et al. and others.

It is common in the practice to employ solid support-based chemistry for these methods. A collection of solid supports are split into individual pools. These pools are then exposed to a series of reactive monomers, followed by a recombination step, in which the position of all solid supports is randomized. The solid supports are then split into a new set of individual pools, exposed to a new series of reactive monomers, followed by a second recombination step. By repeating this split, react and recombine process all possible combinations of oligomer or compounds from the series of monomers employed are obtained, providing a large excess of solid supports are utilized.

The number of oligomer or compounds obtained in an experiment is equal to the product of the monomers employed, however, the number of chemical transformation steps required is only equal to the sum of the monomers employed. Therefore, a geometric amplification of oligomer or compounds is realized relative to the amount of chemical transformation steps employed. For instance, only nine (9) transformation steps were employed using three (3) amino acid monomers in a three step process for the combinatorial synthesis of 27 peptide oligomer.

The prior art split-pool methods produce pools of oligomer or compounds as a product of the experiment. Therefore, the identification of a specific member of the library is typically found by screening the pools for a desired activity, biological or otherwise. The disadvantages of the deconvolution split-pool methods are that (a) the technique always requires that large mixtures of oligomer are screened in bioassays, (b) sequential rounds of resynthesis and bioassay are always required to deconvolute a library, and (c) since single oligomer are not produced a library is always stored as a mixture, requiring later deconvolution.

In the practice of encoded split-pool methods physical separation of the solid support is required to accomplish two tasks: first, to physically isolate the individual library member after screening and, second, to de-code the identity of the tag and thus deduce the chemical structure of the member. A disadvantage specific to the chemically encoded split-pool methods is that chemical tags introduce potential side reactions and failures both with orthogonal linkers and with tags, thus requiring compatibility between the tag chemistry and the chemistry utilized to synthesize the combinatorial library.

In practice, both categories of split-pool methods require a large excess of solid support beads to ensure with reasonable certainty (99% confidence level) that all possible oligomer are made when a random split-pool strategy is employed. This is necessary because the exact identity of each bead (i.e. the identity of each oligomer) is lost due to the unstructured nature of the split-pool method. This presents a significant problem when scaling up these methods for the production of micromole or larger amounts of individual oligomer in the library.

The parent application discloses a technique in the combinatorial chemistry art which can achieve geometric amplification in the number of library members synthesized relative to the number of synthetic steps required but, additionally, (a) avoids the need for chemical encoding steps (b) produces micromolar or larger amounts of individual oligomer; (c) uses only the number of solid supports required for the number of possible oligomer in the library; and (d) produces the oligomer in spatially-dispersed arrays wherein the identity of the oligomer is determined by its location in the array.

There is a need in the combinatorial chemistry art for apparatus which can carry out the processes and methods of the parent application.

There is a need in the combinatorial chemistry art for apparatus which can carry out the processes and methods of producing the oligomer in spatially-dispersed arrays wherein the identity of the oligomer is determined by its location in the array.

Glossary

Monomer: As used herein, a "monomer" is any atom or molecule capable of forming at least one chemical bond. Thus, a "monomer" is any member of the set of atoms or molecules that can be joined together as single units in a multiple of sequential or concerted chemical or enzymatic reaction steps to form an oligomer. Monomers may have one or a plurality of functional groups, which functional groups may be, but need not be, identical. The set of monomers useful in the present invention includes, but is not restricted to, alkyl and aryl amines; alkyl and aryl mercaptans; alkyl and aryl ketones; alkyl and aryl carboxylic acids; alkyl and aryl esters; alkyl and aryl ethers; alkyl and aryl sulfoxides; alkyl and aryl sulfones; alkyl and aryl sulfonamides; phenols; alkyl alcohols; alkyl and aryl alkenes; alkyl and aryl lactams; alkyl and aryl lactones; alkyl and aryl di- and polyenes; alkyl and aryl alkynes; alkyl and aryl unsaturated ketones; alkyl and aryl aldehydes; heteroatomic compounds containing one or more of the atoms of nitrogen, sulfur, phosphorous, oxygen, and other polyfunctional molecules containing one or more of the above functional groups; L-amino acids; D-amino acids; deoxyribonucleosides; deoxyribonucleotides; ribonucleosides; ribonucleotides; sugars; benzodiazepines; P-lactams; hydantoins; quinones; hydroquinones; terpenes; and the like. The monomers of the present invention may have groups protecting the functional groups within the monomer. Suitable protecting groups will depend on the functionality and particular chemistry used to construct the library. Examples of suitable functional protecting groups will be readily apparent to skilled artisans, and are described, for example, in Greene and WUtS,14 which is incorporated herein by reference. As used herein, "monomer" refers to any member of a basis set for synthesis of an oligomer.

For example, the dimers of 20 L-amino acids form a basis set of 400 "monomers" for synthesis of polypeptides. Different basis sets of monomers may be used at successive steps in the synthesis of an oligomer.

Oligomer: As used herein, an "oligomer" is any chemical structure that can be synthesized using the combinatorial library methods and apparatus of this invention, including, for example, amides, esters, thiGethers, ketones, ethers, sulfoxides, sulfonamides, sulfones, phosphates, alcohols, aldehydes, alkenes, alkynes, aromatics, polyaromatics, heterocyclic compounds containing one or more of the atoms of nitrogen, sulfur, oxygen, and phosphorous, and the like; chemical entities having a common core structure such as, for example, terpenes, steroids, P-lactams, benzodiazepines, xanthates, indoles, indolones, lactones, lactams, hydantoins, quiriones, hydroquinones, and the like; chains of repeating monomer units such as polysaccharides, phospholipids, polyurethanes, polyesters, polycarbonates, poly ureas, polyamides, polyethyleneimines, poly arylene sulfides, polyimides, polyacetates, polypeptides, polynucleotides, and the like; or other oligomer as will be readily apparent to one skilled in the art upon review of this disclosure. Thus, an "oligomer" of the present invention may be linear, branched, cyclic, or assume various other forms as will be apparent to those skilled in the art. Thus, "oligomer" may be used synonymously or interchangeably with "compound", thus describing any structure, organic or inorganic, which can be produced in a sequential fashion via the addition of monomeric units as described above.

Solid Support: A "solid support" as used herein is a material, or combination of materials, having a rigid or semi-rigid surface and having functional groups or linkers, or that is capable of being chemically derivatized with functional groups or linkers, that are suitable for carrying out chemical synthesis reactions. Such materials will preferably take the form of small beads, pellets, disks, cylinders, capillaries, hollow fibers, needles, solid fibers, cellulose beads, pore-glass beads, silica gels, polystyrene beads cross-linked with divinylbenzene and optionally grafted with polyethylene glycol, grafted co-poly beads, poly-acrylamide beads, latex beads, dirnethylacrylamide beads optionally cross-linked with N,N'-bis-hycryloyl ethylene diamine, polydimethylacrylainide beads crosslinked with polystyrene, glass particles coated with a hydrophobic polymer, or other convenient forms. "Solid supports" may be constructed such that they are capable of being transferred mechanically from one support carrier to another support carrier.

Linker: A "linker" is a moiety, molecule, or group of molecules attached to a solid support and spacing a synthesized oligomer from the solid support. Typically a linker will be bi-functional, wherein said linker has a functional group at one end capable of attaching to a monomer, oligomer, or solid support, a series of spacer residues, and a functional group at another end capable of attaching to a monomer, oligomer, or solid support. The functional groups may be, but need not be, identical. Additionally, said linker may be cleaved by a chemical transformation such that the synthesized oligomer, or part of the synthesized oligomer, or the synthesized oligomer and the linker, or the synthesized oligomer and part of the linker may be chemically separated from the solid support, linker, or both.

Carrier: A carrier as used herein is a portable support structure or platform which may be in the form of a tray, grid or other form for positionally holding s plurality of solid supports in predetermined spatial arrays. A carrier can take any number of forms suitable for receiving and temporarily holding solid supports in a desirable spatial array. A "donor carrier" is a carrier that is loaded with solid supports and is in a position to transfer the solid supports to a donee carrier. A "donee or recipient carrier" is an empty carrier that is readied or positioned to receive solid supports from a donor carrier.

Column: The term "column" as used herein for the arrangement of the solid supports means a vertical row. That is, column means a row that extends toward and away from the observer or vertically from top toward the bottom of a page.

Row: The term row as used herein for the arrangement of the solid supports means a horizontal row that extends left to right on a page.

SUMMARY AND OBJECTS OF THE INVENTION

A primary object of the present invention is to provide an apparatus and method for the synthesis of a spatially-dispersed combinatorial library of oligomer, in which the oligomer are distributed in a controlled manner.

In accordance with a primary aspect of the invention, a system for moving multiple supports in parallel through multiple different synthesis steps to provide a library of oligomer comprises at least two monomers, a plurality of synthesis supports, a first plurality of support carriers wherein each carrier has a uniform array of distinct support holding positions for said synthesis supports, means for contacting each array of synthesis supports with a different monomer to provide a first chemical transformation of said synthesis supports, a second plurality of support carriers wherein each carrier has a uniform array of distinct support holding positions for receiving said chemically transformed synthesis supports contained in said first plurality of support carriers, transfer apparatus for transferring a selected row or column of synthesis supports from each of said first plurality of carriers to each of said second plurality of carriers to enable the supports in the second to undergo at least a second chemical transformation, and whereby each support position in each carrier identifies the chemical compound thereon.

An object of the present invention is to provide an improved apparatus and method for the synthesis of a spatially-dispersed combinatorial library of oligomer, in which the oligomer are distributed in a controlled manner. These oligomers are comprised of a series of monomers which are introduced into the oligomer in a sequential and stepwise fashion via chemical transformation steps (hereafter referred to as "steps"). These monomers are comprised of subsets of monomers such that the first subset of monomers is introduced in the first step, the second set of monomers is introduced in the second step, etc. The method further comprises apparatus for holding a plurality of solid supports in a sequence of spatial arrays during steps of chemical transformation steps and moving them in a sequential and stepwise fashion between transformation steps. The method comprises means for introducing the monomers in a sequential and stepwise fashion on a series of solid supports. The number of supports equals the number of oligomer in the library.

A novel aspect of this apparatus and process as distinguished from the prior art is that the supports are arranged in, and subsequently redistributed in a controlled manner between, a series of arrays. This series of arrays are enabled by means for holding the supports in physically discrete locations such that the exact identity of each support is provided by its location. The series of arrays of supports are placed in a further series of reaction vessels for the individual steps of an oligomer synthesis. After each step in the oligomer synthesis the supports are redistributed in a predetermined controlled manner from one series of arrays to a next series of arrays.

A further novel aspect of this process is that between each step the redistribution of the supports is carried out in a controlled fashion, such that all possible combinations of possible oligomer are synthesized. A further novel aspect of this process is that the positions of all supports are known during the synthesis experiment such that the identity of an oligomer is unequivocally established by its physical location. Thus, the applied method achieves a geometric amplification in the number of library members synthesized relative to the number of synthetic steps required while providing individual library members in a spatially dispersed format. Thus, the use of a tagging system is eliminated for a split-pool synthesis experiment.

The apparatus and method has utility in the production of oligomer which are available for screening in assays for novel biological, chemical, or physical properties which may have commercial value. Further, the structures of these oligomer are readily identifiable by virtue of their physical location. The apparatus further provides a means for producing each oligomer in a discrete physical location which allows any pre-determined oligomer to be readily isolated from all other oligomer in the library. Yet another advantage of the invention is that no excess of solid supports is required, thus enabling a larger scale of synthesis.

BRIEF DESCRIPTION OF THE DRAWINGS

The above and other objects and advantages of the present invention will be appreciated from the following specification when read in conjunction with the accompanying drawings wherein.

DETAILED DESCRIPTION OF THE PREFERRED EMBODIMENTS

The system and method described herein is suitable for the synthesis of a library of oligomers comprised of two, three, or more sets of oligomer. However, the system described is most suitable for the synthesis of a library of oligomers comprised of three monomer subsets. The sums of monomers in each of these subsets may be variable. However, conveyance of the methodology to those practiced in the art may be initially illustrated when the sum of all monomers in each subset is equal. The sum of monomers in each subset is defined by n in which n is a positive integer. The solid supports are preferably arranged in a series of arrays of dimension n×n on suitable carriers. There are a total of n such arrays required for the synthesis of such a library. Therefore, the total number of oligomer in a three step synthesis is the product n×n×n.

The n arrays of solid supports are preferably arranged in support carriers (hereafter referred to as "carriers'). Each carrier holds an n×n array of solid supports. Alternatively, several carriers may be used to hold an n×n array of supports. However, preferably the carriers are of sufficient size to hold an entire n×n array of supports. Thus, preferably there are n carriers which are placed in n reaction vessels for each chemical transformation step such that each individual monomer from a subset of n monomers is reacted with the supports in each individual reaction vessel.

Figure 1:
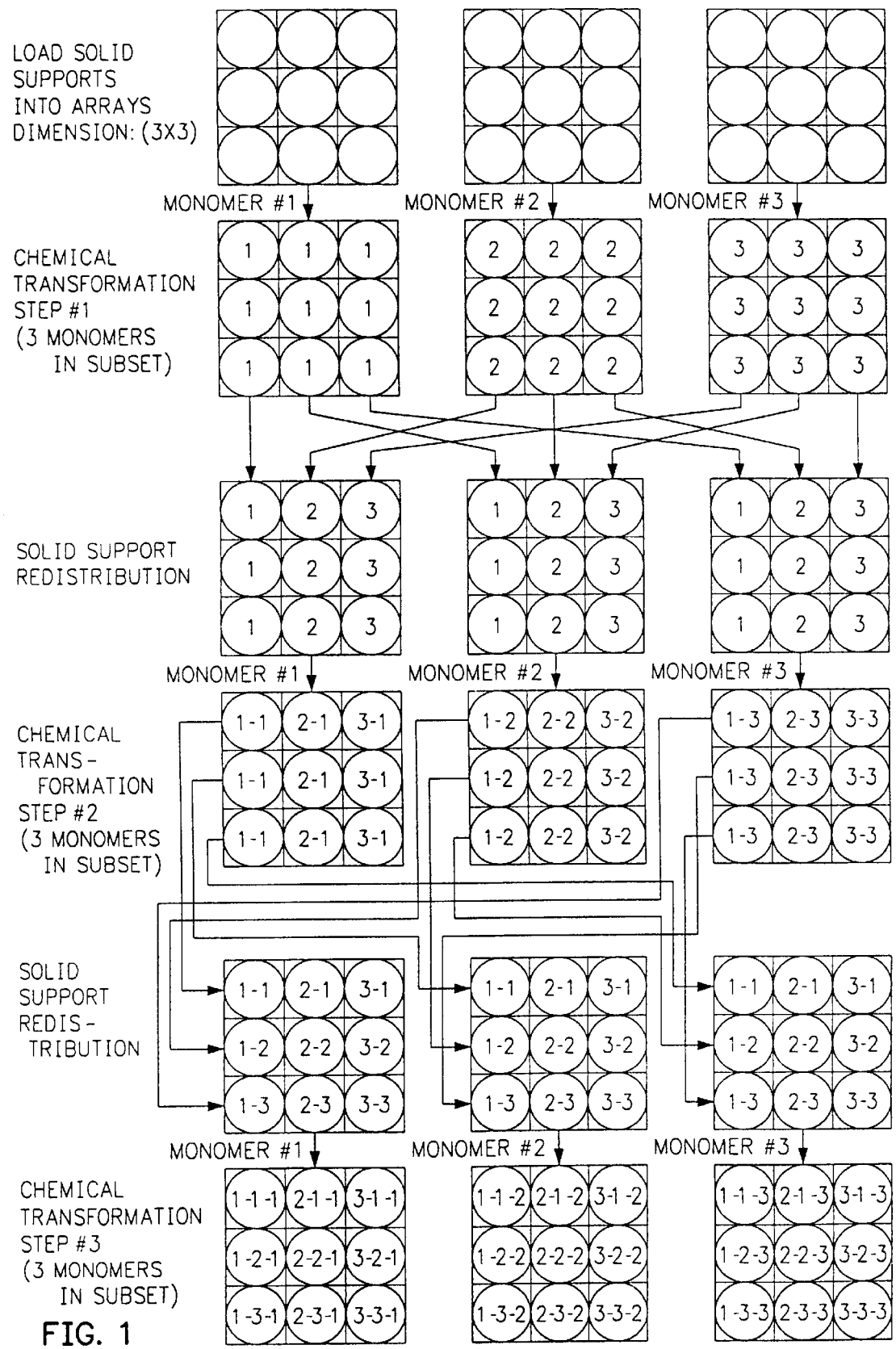
FIG. 1 is a schematic illustration of a flow diagram for a three by three array through a three step chemical transformation.

A further novel aspect of this system and process as distinguished from the prior art is the system and method by which the supports are redistributed from one series of arrays to the next series of arrays between chemical transformation steps. This novel method is illustrated in FIG. 1 for a three-step combinatorial synthesis using three subsets of monomers, each subset containing three monomers (i.e. n=3), to produce a library of 27 (i.e. n×n×n=27) oligomer. The supports are arranged as arrays of rows and columns on the carriers and reacted with a first subset of monomers.

After chemical transformation step #1, the columns of supports in the first series of arrays are redistributed such that the first column from the first array in the first series is transferred to the first column of the first array in the second series; the second column from first array in the first series is transferred to the first column of the second array in the second series; the third column from the first array in the first series is transferred to the first column of the third array in the second series. The first, second and third columns of supports from the second and third arrays in the first series are redistributed to the second series of arrays for chemical transformation step #2 in a similar fashion.

After having completed this redistribution process, the arrays of supports undergo chemical transformation step #2. After step #2 the arrays are redistributed again to a new series of arrays. The method of redistribution is similar to that used after the chemical transformation step #1, however, it is the individual rows of each array that are redistributed rather than the columns described above.

The redistribution as described above is shown in FIG. 1. Thus, the rows of supports in the second series of arrays are redistributed such that the first row from the first array in the second series is transferred to the first row of the first array in the third series; the second row from first array in the second series is transferred to the first row of the second array in the third series; the third row from the first array in the second series is transferred to the first row of the third array in the third series. The first, second and third rows of supports from the second and third arrays in the second series are redistributed to the third series of arrays for chemical transformation step #3 in a similar fashion.

It should be noted that the redistribution of supports between the chemical transformation steps #1 and #2 and between steps #2 and #3 is functionally identical if one simply reorients the arrays such that rows become columns and columns become rows (such as accomplished by a 90 degree rotation). If such a reorientation of the second series of arrays occurs then the columns from the second series of arrays are redistributed to columns in the third series of arrays. Following this second redistribution, chemical transformation step #3 is carried out on the supports. Using this redistribution method, all 27 possible combinations of monomers are ensured thus producing a combinatorial library of 27 oligomer.

It may be appropriate to indelibly mark the carriers which hold the arrays using a means to ensure that rows are recognized as distinct from columns in each array. Additionally, each carrier may also be indelibly marked to distinguish the contents of its arrays uniquely from other carrier's arrays. Preferably, a barcode reading device may be used to query this information from a barcode placed across the top of the columns or beside the rows of each carrier.

As appreciated by those familiar in the art, this redistribution method for an n×n×n library is efficient, transferring entire columns or entire rows of supports simultaneously. The synthesis of these 27 oligomer was accomplished with three chemical transformation steps involving a total of only 3 individual reaction vessels for each step. The products from the library synthesis experiment are held in discrete locations, thus allowing for the identification and isolation of each individual library member. Additionally, this redistribution method is amenable to automation via robotics.

The above illustration describes a method for synthesizing a library of oligomer of very modest size. The technique is readily extrapolated to the synthesis of much larger libraries, e.g. one million oligomer using a three step synthesis with arrays of dimension 100×100 supports, 100 carriers, 100 monomers in each step. Thus a total of 100 reaction vessels can be employed to produce a library of one million members, all spatially-dispersed, individually identifiable and individually isolated. Those practiced in the art will appreciate that spatially-dispersed techniques as previously practiced by Geysen, Cody, and Ellman's would have required 3 million reaction vessels to produce an identical resulting oligomer library.

In order to further illustrate the practice of the present invention, a system and apparatus are illustrated for carrying the methods and process of the invention. While these examples illustrate methods for three combinatorial steps, the methods may be extended to synthesize combinatorial libraries which require more than three combinatorial steps as will become obvious to those persons skilled in the art. In addition, the methods may be carried out using unsymmetrical arrays as will be apparent to those of skill in the art.

Figure 2:
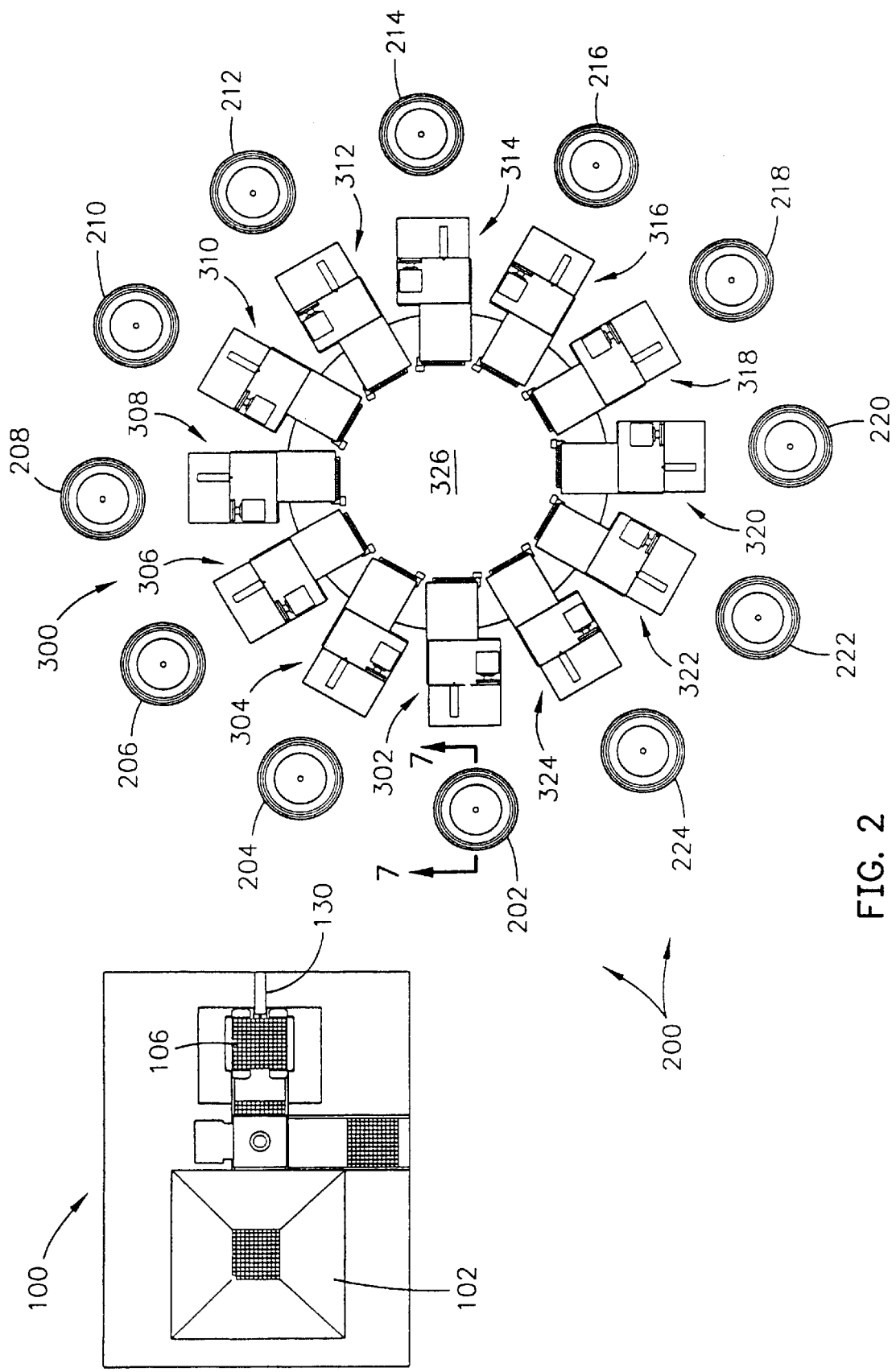
FIG. 2 is a top plan view of a system in accordance with an exemplary embodiment of the invention.
Figure 3:
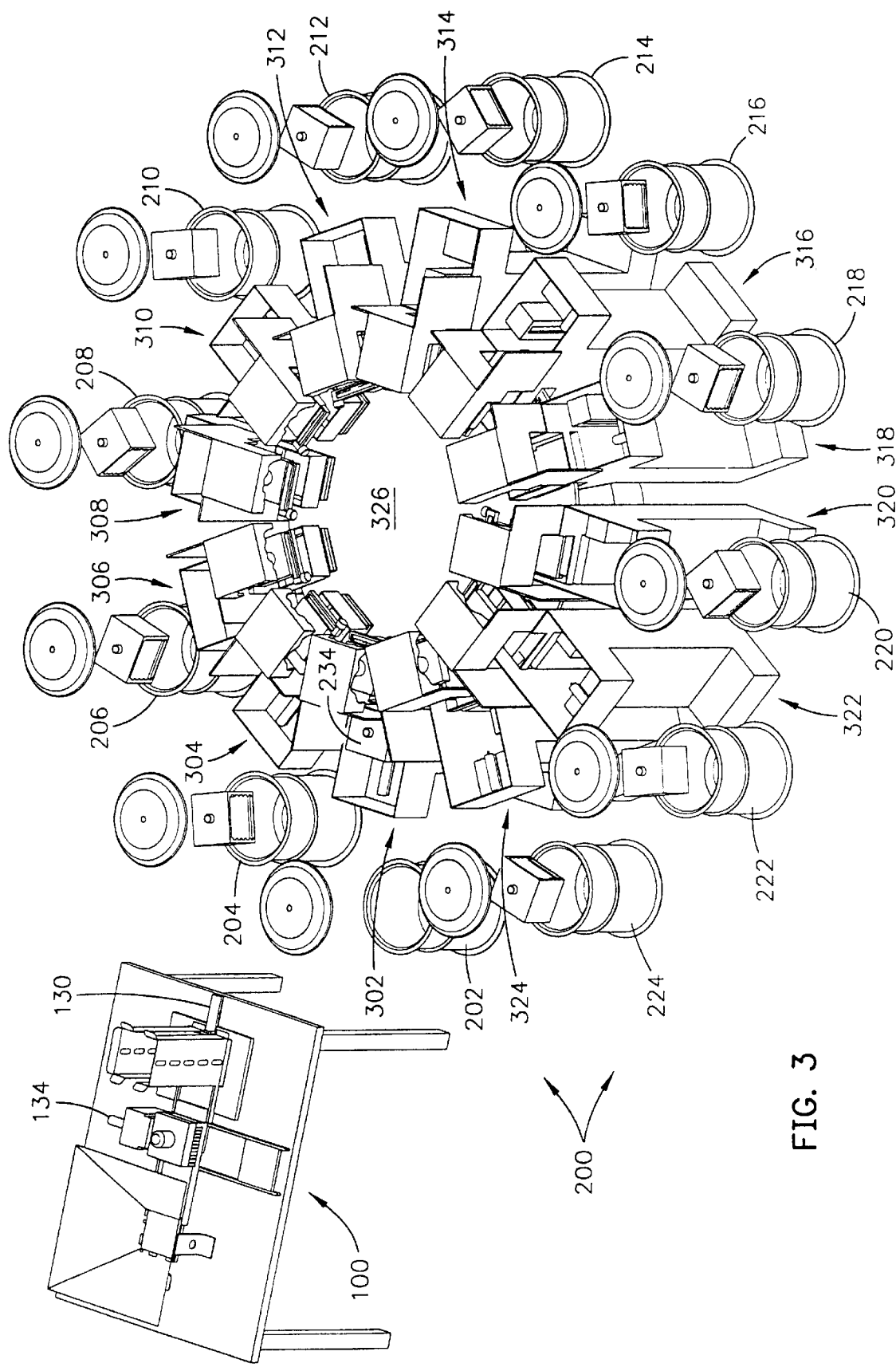
FIG. 3 is a perspective view of the system of FIG. 2.

An exemplary embodiment of a suitable system carrying out the steps and methods of the aforementioned process for practice of the present invention is schematically illustrated in FIGS. 2 and 3 and designated generally by the numeral 10. The process can be carried out in any number of different ways with the steps carried out partially or entirely automatically by machine and/or partially or entirely manually. The illustrated system comprises three main subsystems. These comprise a solid support loading system or unit 100, a reaction chamber system or unit 200 and a redistribution system or unit 300. The solid support loading system, designated generally at 100, comprises a solid support source, a support carrier or carrier source and means for loading the solid supports into the support carriers. The reaction chamber system, designated generally 200, comprises an array of reaction chambers to receive the supports for a series of chemical transformations. The transfer and redistribution unit, designated generally 300, comprises a transfer unit for each reaction chamber which works in conjunction with a conveyer system to transfer and redistribute the solid supports in a predetermined controlled fashion from carriers to subsequent carriers for subsequent chemical transformations. The multiple supports move in a predetermined controlled fashion in parallel from carrier to carrier through multiple different synthesis steps to provide a library of oligomer comprising at least two monomers wherein the oligomer are identifiable by their location or position in the carriers of the system. This predetermined systematic transfer or redistribution of the supports from carrier to carrier through the many steps of the process ensures that any oligomer can be identified by the location of its support at any time in the system.

Figure 4:
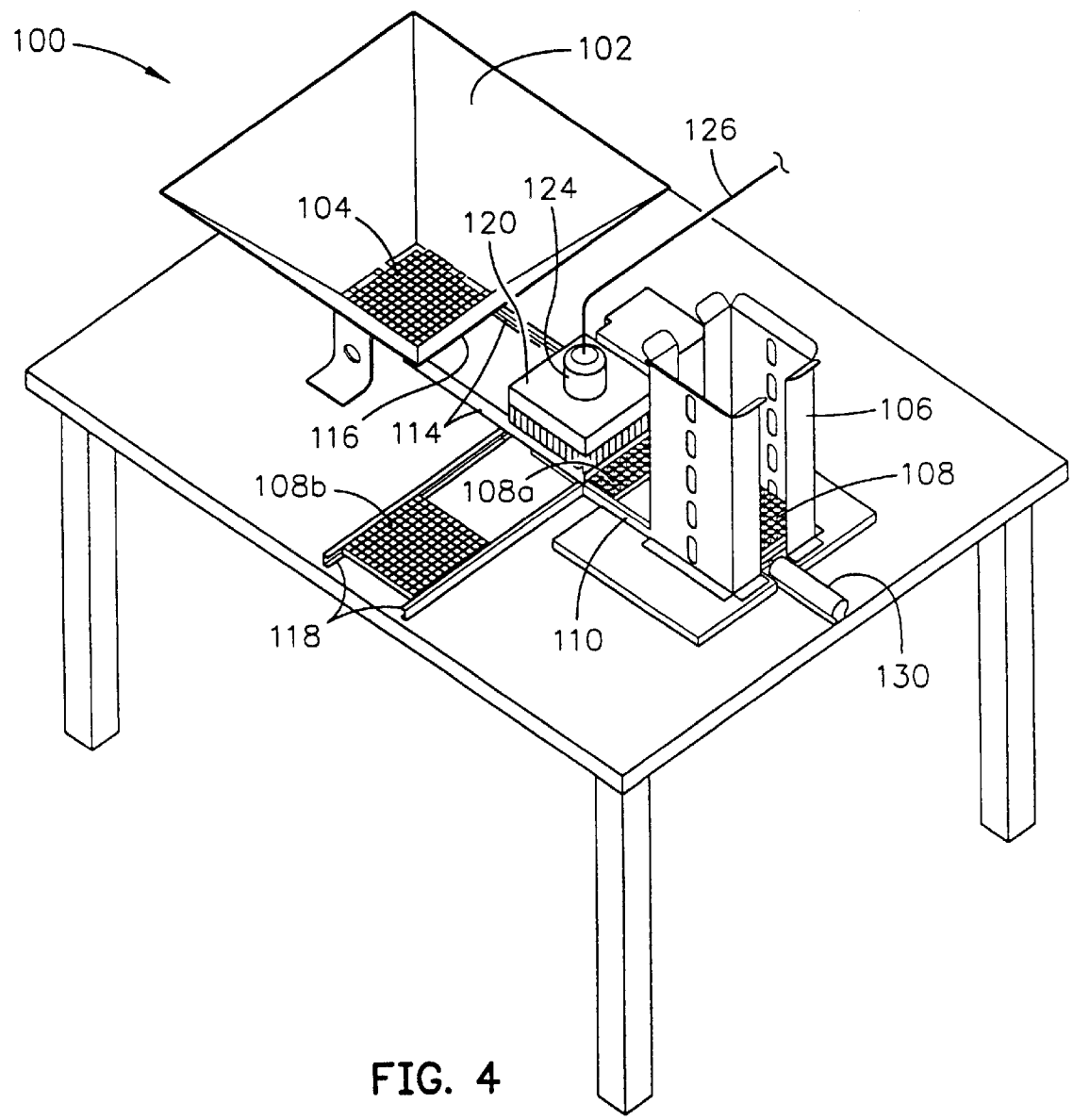
FIG. 4 is a perspective view of the support to carrier loading apparatus of the system of FIG. 2.
Figure 5:
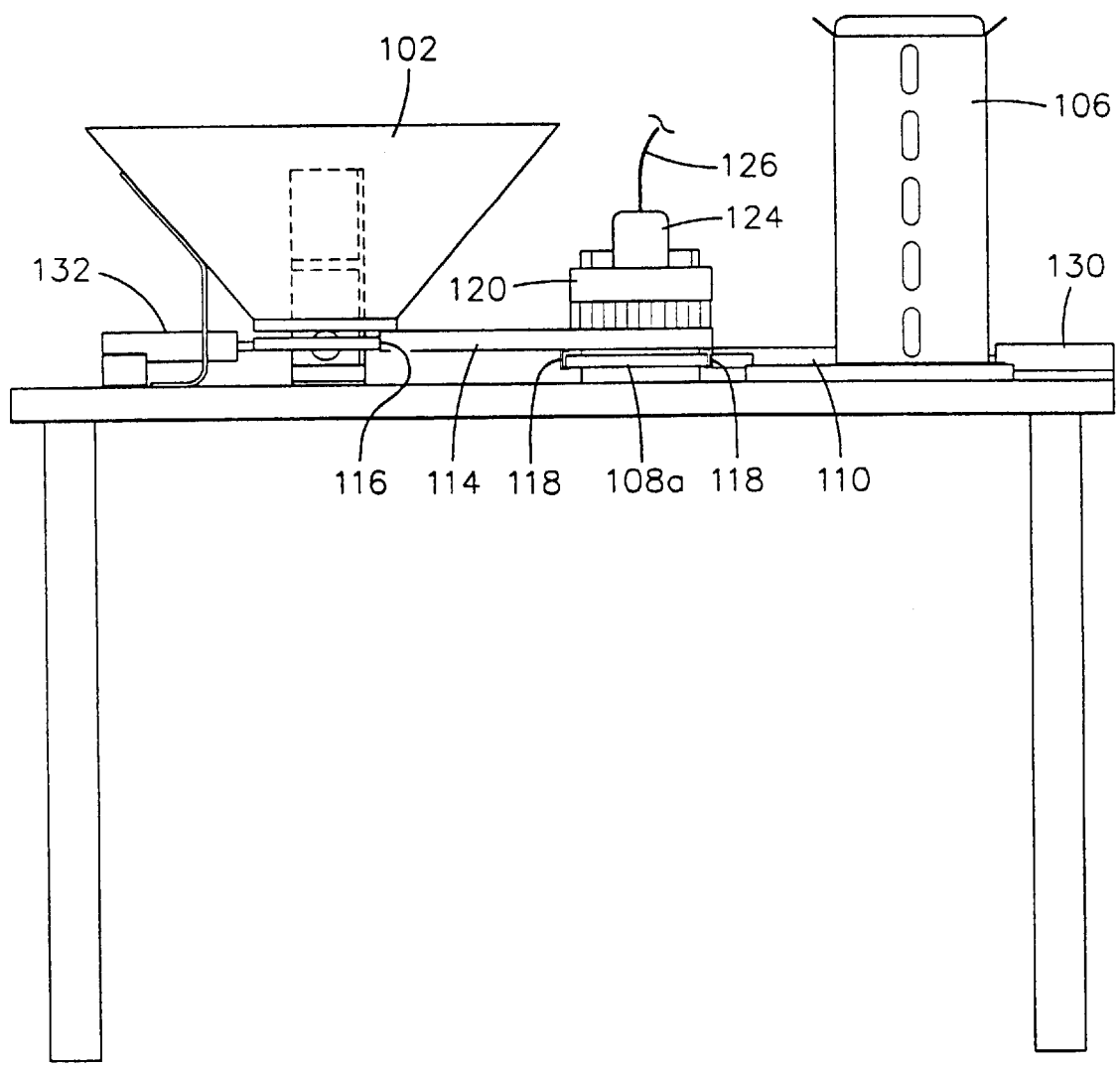
FIG. 5 is a side elevation view of the apparatus of FIG. 4.

The solid support loading system, as best illustrated in FIGS. 4 and 5, comprises a hopper 102 for containing source or supply of solid supports on which chemical transformation is to be carried out for loading into support carriers. The hopper 102 has upstanding sloped sides sloping downward and converging to a bottom central opening 104 which may preferably have a grid like pattern of openings matching the openings in a shuttle carrier. A generally box like upstanding chute 106 is adapted to hold a supply of a plurality of carriers 108 for receiving and mounting the solid supports. A track comprising a pair of spaced apart rails 110 connect the chute 106 to a central transfer position beneath a transfer punch mechanism designated generally at 112 where solid supports are loaded from a shuttle onto or into the supports. An upper track comprising a pair of rails 114 guide a transfer shuttle 116 from the hopper 102, where it is loaded with solid supports, to the central transfer position where the solid supports are transferred to the carriers. The shuttle moves to a position above a carrier where the punch transfers the supports from the shuttle to the carrier. Loaded carriers are transferred along a track comprising a pair of spaced rails 118 to a reaction chamber or to a position to be retrieved for transfer to a reaction chamber. The carriers 108 are moved by suitable means such as a pneumatic ram 130 to the transfer position beneath transfer punch 112. An actuator such as a pneumatic cylinder 132 moves the shuttle 116 back and forth between a support loading position beneath hopper 102 and a transfer position beneath the transfer punch 112. Loaded carriers may be pushed out along track 118 from beneath the transfer punch by suitable transport means such as a pneumatic ram 134.

The solid support transfer mechanism comprises a housing or head 120 in which is mounted a vertically reciprocating plunger having a plurality of vertically oriented punch pins 122. The reciprocating plunger in head 120 is operated by a suitable power unit such as a linear motor which is preferably a pneumatic cylinder 124 via a line 126 to a suitable pressurized air source. It may also be operated by an electrical solenoid or other suitable linear motor. The power unit 124 operates to move the plunger vertically downward to transfer the solid supports from the shuttle to the receiving carrier. The plunger has a plurality of pins in lines corresponding to the holding positions of the solid supports in the shuttle and carriers.

The system includes a plurality of reaction chambers 200 sufficient in number to carry out the desired reactions and produce the required number of oligomer. In a preferred system, the reaction chambers will be in a uniform array and which is preferably a circular array. This provides an array that is easy to service with a transport mechanism such as a turntable or carousel and other devices such as an automatic manipulating system. It also provides a continuous loop path for the carriers as opposed to a linear array, which would have a beginning and an end such that the carriers would have to be transported from the end back to the beginning.

The system includes an array of reaction chambers suitable in number to carry out the desired reactions, 202, 204, 206, 208, 210, 212, 214, 216, 218, 220, 222 and 224 shown in a circle. The loaded support carriers are transported either manually or by suitable conveyor or other means to the respective reaction chambers 202, 204, 206, 208, 210, 212, 214, 216, 218, 220, 222 and 224. In a preferred arrangement, the system has 12 reaction chambers and the support carriers that will be fed or loaded into the chambers are either 12 in number or multiples thereof The carriers define an array of the solid supports as used herein. An array may be defined by a single support (e.g. a 12×12 support) or by a plurality of the supports such as four 12×12 supports to define a 24×24 array.

Figure 6:
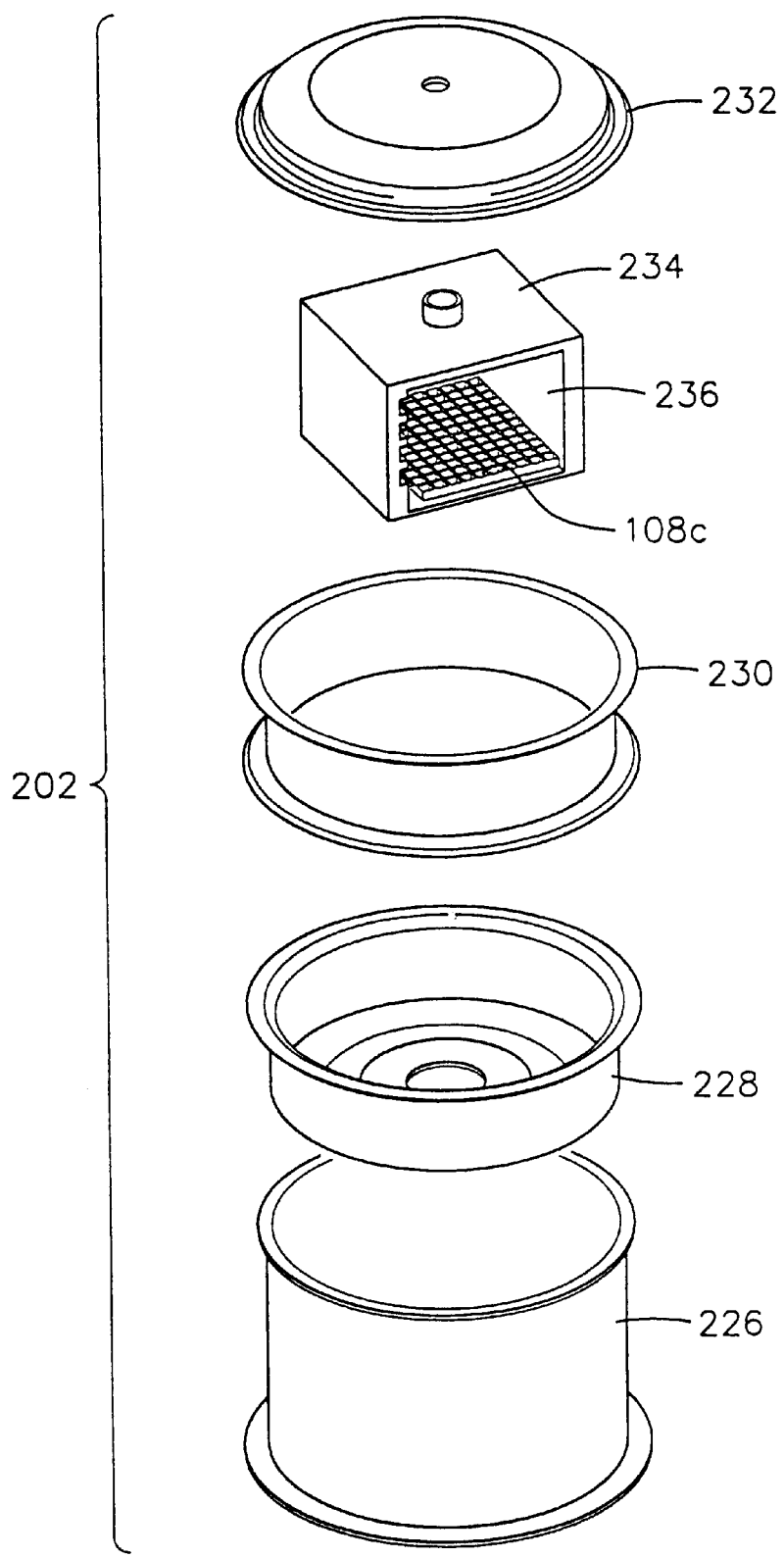
FIG. 6 is an exploded view of a reaction chamber of the system of FIG. 2.
Figure 7:
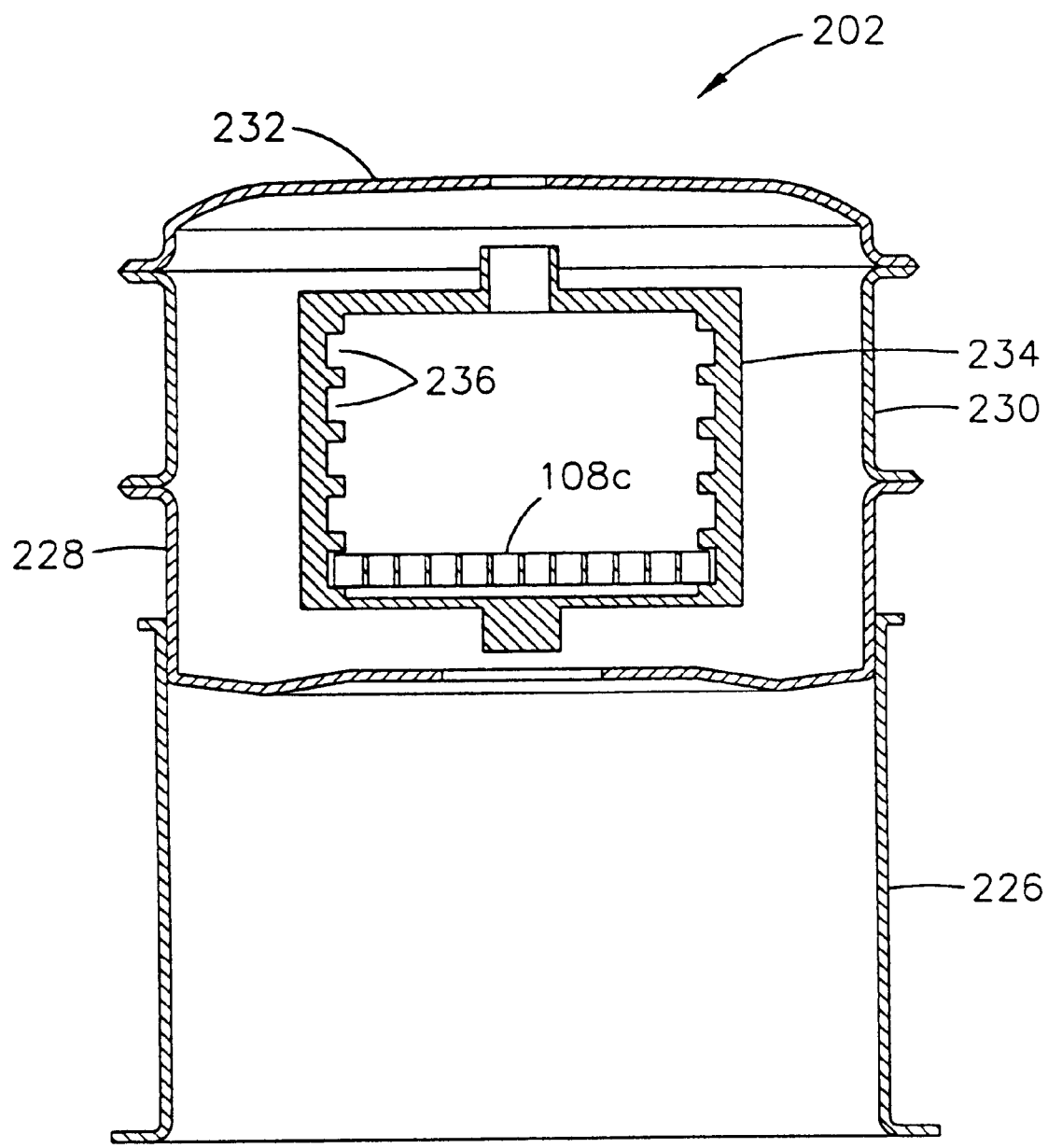
FIG. 7 is a side elevation view in section of the reaction chamber taken on line 7—7 of FIG. 2.

The illustrated system includes an array of twelve reaction chambers, but could have more or less. The reaction chambers are identical, and only one will be described in detail. A reaction chamber 202, as best illustrated in FIGS. 6 and 7, comprises a generally cylindrical base 226 on which is mounted a cylindrical vessel. The vessel may be a single cylindrical unit 228 or a double unit including a second section or extension 230 and a removable cover or closure 232. The extension 230 enables the vessel to be enlarged to accommodate a large carrier rack 234 with multiple carriers. The rack 234 is designed with vertically spaced horizontal slots 236 to receive up to five carriers. This enables the loading of four filled or loaded carriers and an empty carrier to use in the redistribution steps as will be explained. An empty carrier 108c is shown in the bottom slot of the rack.

The redistribution system 300 is disposed in the center of and surrounded by the circular array of reaction chambers (FIGS. 2 and 3). Each of the reaction chambers is provided with a transfer apparatus or unit 302, 304, 306, 308, 310, 312, 314, 316, 318, 320, 322 and 324 each of which includes means for receiving a carrier rack and means for transferring the supports from carrier to carrier. The redistribution system 300 also includes a conveyor or transporting mechanism which, in the illustrated embodiment, comprises a carousel or rotating table 326 having carrier holding positions or stations such as a recess to receive and hold a carrier aligned for each transfer unit. The carousel operates to transport once-empty carriers from station to station for receiving predetermined rows or columns of supports from a loaded carrier.

Referring to FIGS. 8A–8D, associated with each reaction chamber is a shuttle or support transfer apparatus as illustrated, and designated generally at 300. The transfer devices are all identical and only one of which 302 will be described in detail. The transfer devices comprise a vertical support stand 328 having a solid support transfer head 330 having a carrier to carrier transfer mechanism therein. The solid support transfer mechanism comprises a support member 332 mounted on a rotary member or shaft 334 having a reciprocating plunger with a plurality of transfer punch pins 336 mounted thereon. The number of pins 336 are equal in number to the solid support positions in a row or column in a carrier. The pins are moved vertically by a suitable linear actuator such as a pneumatic cylinder in shaft member 334. The shaft 334 is rotated or indexed 90 degrees by a motor 338 through a timing belt drive 340 to selectively position or orient the pins 336 for transferring a selected column or row of solid supports.

Figure 8A:
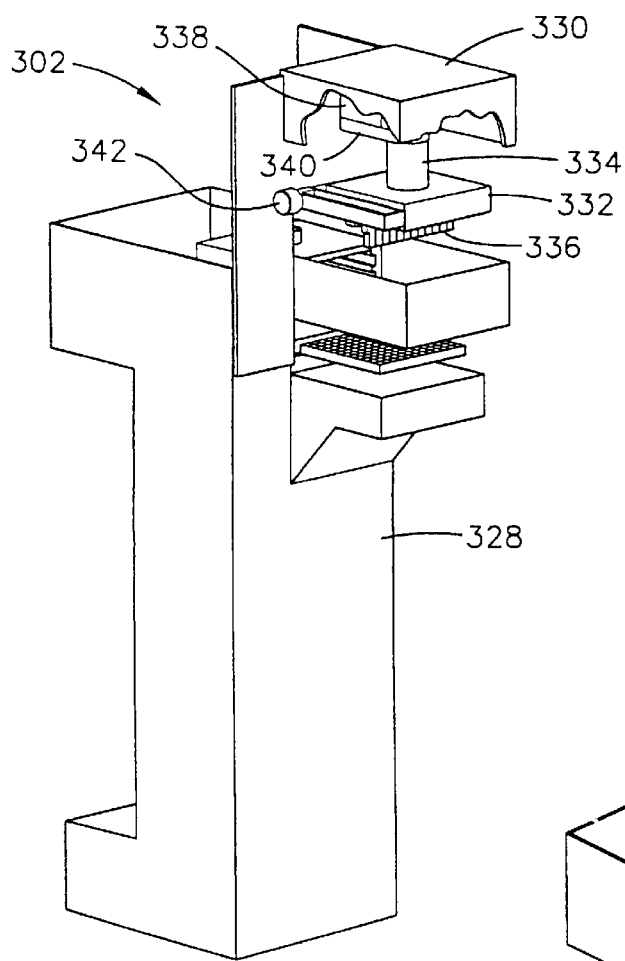
FIG. 8A is a perspective view of the support carrier to carrier transfer apparatus of the system of FIG. 2 showing the support transfer device in one orientation.
Figure 8B:
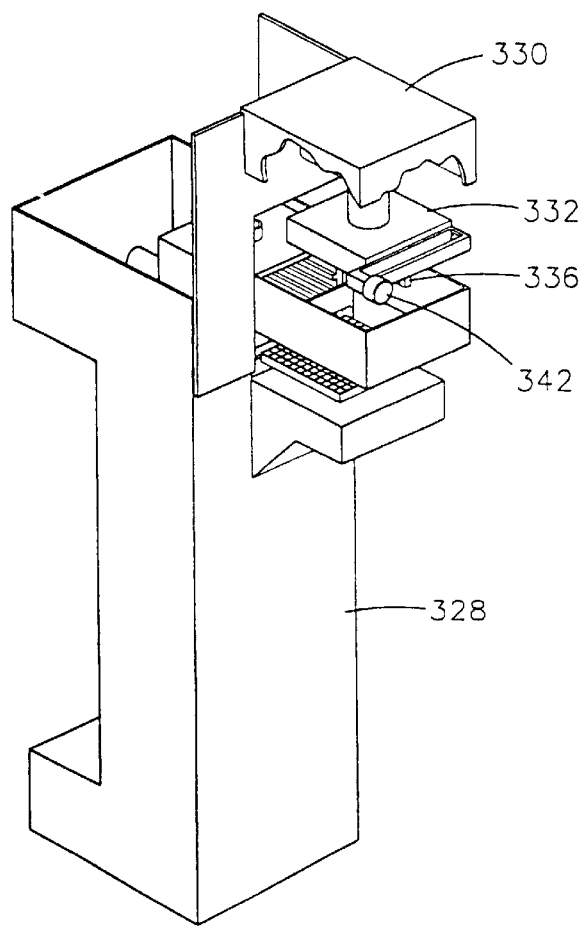
FIG. 8B is a view like FIG. 8A showing the support transfer device in another orientation.
Figure 8C:
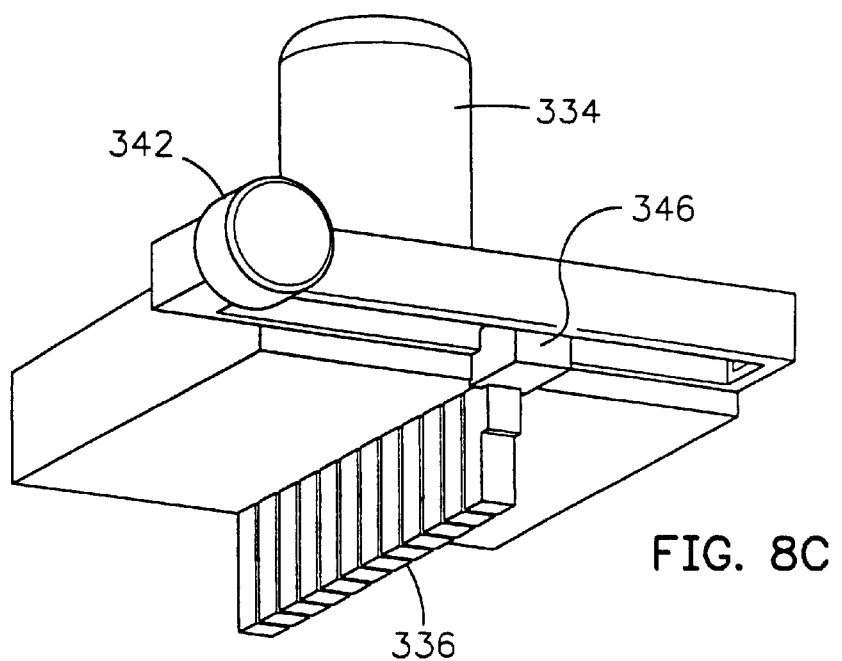
FIG. 8C is a perspective view from below of the carrier to carrier transfer head of the apparatus of FIG. 8A.
Figure 8D:
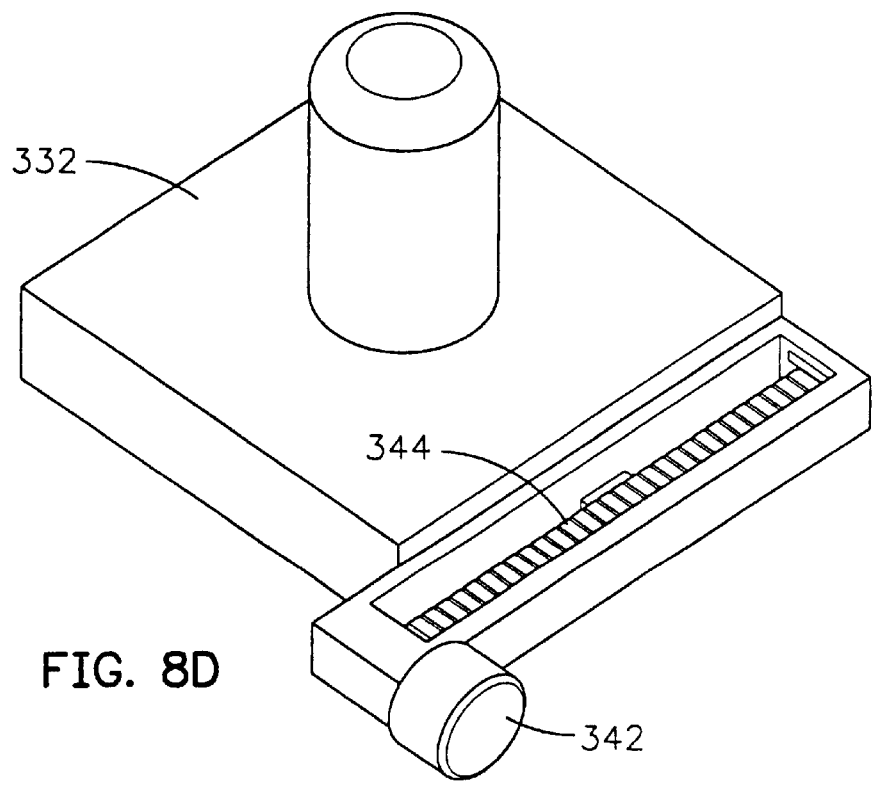
FIG. 8D is a perspective view of the carrier to carrier transfer head of the apparatus of FIG. 8A.

The punch pins 336 are laterally positioned to a selected one of a column or a row by a suitable drive mechanism such as a motor 342 driving a belt or rack 344 (FIG. 8D). The pins 336 are mounted on a moveable carriage or slide 346 (FIG. 8C) which is connected to and moved by belt or chain 344. The power unit such as a pneumatic cylinder operates to move the plunger vertically to transfer the solid supports from a loaded carrier to a receiving carrier. The plunger has a plurality of pins in lines corresponding to the holding positions of the supports in the carriers.

Figures 9A, 9B:
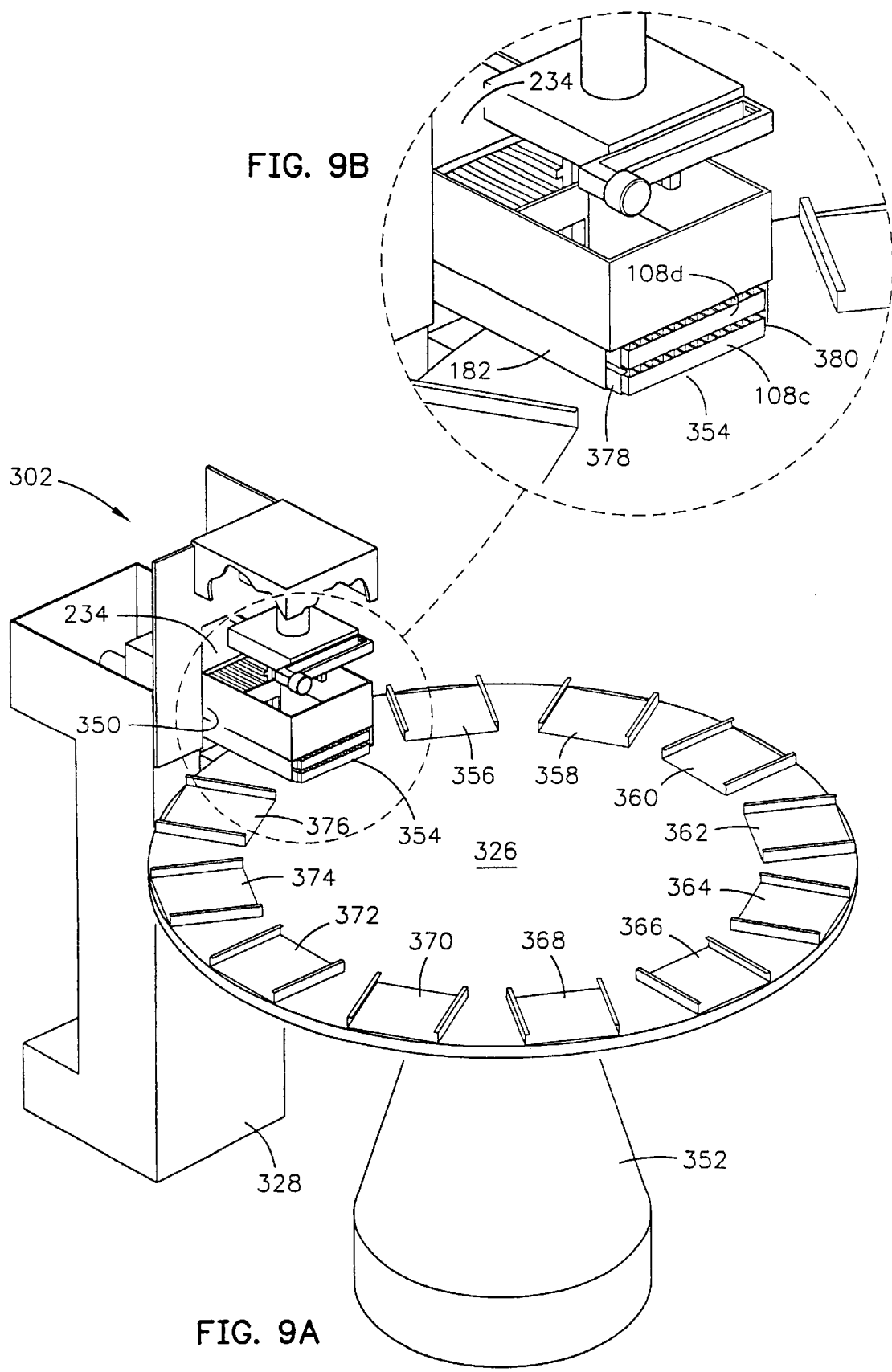
FIG. 9A is a perspective view of the carrier to carrier transfer apparatus of FIG. 8A and the transport carousel.
FIG. 9B is an enlarged partial view of the transfer head of the carrier to carrier transfer apparatus of FIG. 9A.

As illustrated in FIG. 9A, a transfer unit 302 has an elevator platform 350 mounted centrally within support 328 for receiving a carrier rack 234. The elevator platform is raised and lowered by a suitable means such as a stepping motor or air power cylinder (not shown). Any number of suitable elevating mechanisms may be utilized such as pneumatic or hydraulic cylinders, electrical solenoid or a stepping motor device. For example, a stepping motor drives a rack to raise and lower the platform. A shuttle mechanism such as a pneumatic ram 356 is mounted on the head and operative to shuttle or move carriers from the rack 324 onto a track positioned under the solid support transfer head 330.

The solid supports are loaded on or in the carriers in or with predetermined arrays, preferably of rows and columns, which may be equal or unequal. The loaded carriers are then transported from the support loading system either manually or by suitable means such as a conveyor or the like to the respective chemical reaction chambers in the system where the chemical transformations take place. The support carriers may have any suitable configuration but are preferably square with a 12×12 array sized and configured in order to cooperatively work with standard microtiter trays. Thus, oligomers can be transferred directly from supports in the carrier to microtiter trays for evaluation or further processing. The typical microtiter trays have an 8×12 configuration, so that supports from two carriers would be transferred to three microtiter trays.

In the illustrated system, as shown in FIGS. 9A and 9B, the carousel 350 comprises a circular table top mounted for rotation atop a pedestal 352. A drive motor, not shown, drives or steps the top to position the carriers to the transfer positions. The carousel top is preferably equipped with holders such as shown at 354–376 to receive and hold or register the carriers in position for the transfer. The holders may take any suitable form but, are preferably identical and only one, 354, will be described. The holder 354 is secured to the carousel top and includes a track formed of opposed grooved side rails 378 and 380 in which a carrier 108 is slideably received and held in position to receive supports. The holder may include stops or detents (not shown) to precisely position the carrier.

In preparation for transfer of solid supports from carriers from the reaction chamber, empty carriers will be placed on the carousel in preparation for receiving supports from the loaded carriers in the reaction chambers. In the illustrated embodiment, an empty carrier 108c is initially loaded in the rack and transferred from the rack to the holder 354 on carousel 326 when preparing for the transfer. When the reaction and all processing is complete and the supports are ready for transfer or redistribution, the carriers containing the supports on which transformation has occurred will be transported from the respective reaction chamber to a position at the transfer station above the carriers on the carousel. At this point, a transfer mechanism or implement preferably in the form of a punch as previously described, will move a selected one of either a column or row of supports from the loaded carrier to the empty carrier. Hereinafter these carriers may be designated the "donor carrier" and the "recipient carrier".

The solid supports may take any suitable form for optimally supporting chemical transformations and for ease of handling in conjunction with suitable carriers such as support carriers. The support carriers may take any suitable form but are preferably of a configuration which will easily receive the solid supports and hold them in a fixed position to permit them to be handled or loaded into reaction chambers and the solid supports transferred or redistributed from carrier to carrier in preparation for each chemical transformation. The loading of the carriers by the loading system may be by robotics or other automatic means or it may be manual.

In a preferred sequence of redistribution, row 1 will be transferred from the loaded donor carrier at the first transfer station 302 to row 1 in the recipient carrier at that station, while row 2 is transferred from the loaded donor carrier at the second transfer station 304 to row 2 in the recipient carrier at that station, row 3 is transferred from the loaded donor carrier at the third transfer station 306 to row 3 in the recipient carrier at the third transfer station 306 and so on around the array. Thus, when the first transfer has occurred, the first recipient carrier will have a first row, the second recipient carrier will have a second row, the third recipient carrier will have a third row, the fourth recipient carrier will have a fourth row, and so on around the array. These transfers are preferably made simultaneously but may be made in sequence.

Thereafter, the carousel is operated by rotating it either clockwise or counter clockwise, preferably clockwise, to move or transport the carriers one station so that a second transfer can be accomplished. At the same time the transfer punches at each station is moved over one column or row in position to transfer the next column. When the second transfer is initiated, assuming a clockwise rotation, at the first transfer station 302, row 2 will be transferred from the loaded donor carrier at the first transfer station 302 to row 2 in the recipient carrier, while row 3 is transferred from the loaded donor carrier at the second transfer station 46 to row 3 in the recipient carrier, row 4 is transferred from the loaded donor carrier at the third transfer station 302 to row 4 in the recipient carrier at the third transfer station 306 and so on around the array. Thereafter, the carousel is indexed one more position and column 3 is transferred at position 1, column 4 transferred at position 2, column 5 is transferred at position 3 and so on around the system. This continues until all columns or rows in the donor carrier have been transferred to the columns in the recipient carriers. At this stage each recipient carrier has twelve individual columns and/or rows. These carriers are now moved to the respective reaction chamber for a second chemical transformation.

While this transformation is taking place, empty carriers may then be loaded on the carousel in readiness for the next transfer or redistribution. Preferably empty carriers are carried along with the carriers in the rack. Upon completion of the next chemical transformation, the carriers are moved from the reaction chamber to the transfer stations and again, the previously described sequence of transferring columns or rows is carried out. In the event the two transformations is to occur for the particular library at this juncture, the rows are transferred as opposed to the columns. This can be carried out by indexing the donor carriers of 90° in the same direction or alternatively indexing the transfer punches. Once this transfer has occurred, carriers are again returned to the reaction chambers for the next or final transformation. After the transformations are complete, the position of the support in the system identifies the oligomer on the support. At the end of this action, each of the target carriers have 12 different columns that were donated from the 12 different reaction stations. It will be appreciated that other sequences of redistribution can be made so long as they are uniformly followed. For example, all columns 1 can be transferred to a first recipient carrier while all columns 2 can be transferred to a second recipient carrier and so on.

In a system as described with 12 carriers with 12×12, the result is 1,728 oligomer in the library. Thus, by knowing exactly which chemical was in which of the 12 reaction chambers and the sequence in which these solid supports were exposed to those chemicals, allows one, at a subsequent time, to enter a particular support by number and the position by column and row and know exactly which chemical it has been exposed to.

With this system, if one wishes to carry out the process with additional carriers such as, for example, a 24×24 array, the process is carried out in the same manner. However, instead of putting in only a single carrier in each reaction chamber, a stack of four 12×12 carriers are loaded with supports plus an empty carrier are placed in each chamber so that those 4 carriers give a 24×24 array which, in each 24×24 array of supports into 24 reaction chambers, yield 13,824 discrete compounds. In the actual process after the first chemical reaction takes place, the stack of 4 carriers in place in the reaction chambers are washed and dried. When the first chemical transformation is completed and it is ready to transfer to the donee or target carrier, the racks from the chambers are loaded into the transfer stations. A first empty carrier from each reaction chamber is put into place on the carousel for transfer of columns or rows from a donor to a donee or target carrier. Once these have been transferred as in the prior described sequence as the transfer occurs, the carousel would advance only to 12 positions, not 24. Now, at that point, the carousel is backed up to position 1 again. The empty carriers are then moved onto the carousel as the target carriers and then indexed and columns 13–24 are transferred so that one continues where one left off for the other 12 columns. This is repeated for carriers three and four. The number of reaction chambers preferably equal the number of carriers but at least equal the number of arrays.

As is apparent from the above-described general system, first of all, the carousel type of array is a preferred system because it is a continuous system. On the other hand, while a linear system may be preferred in some instances, a linear system would require that a carrier at the end of the line be brought back to the beginning of the line to continue.

It will also be apparent that, with this system, multiples of 12 carriers can be handled even with only a 12 position carousel. Where the carousel has a position for each reaction chamber, the carousel need only move through 12 positions for a complete transfer. A 24×24 array produces 13,824 discrete compounds.

Figure 10:
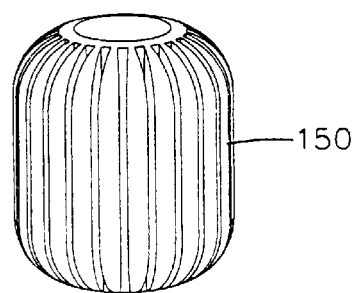
FIG. 10 is a perspective view of an exemplary embodiment of a solid support for use in the system of FIG. 2.

Referring to FIG. 10, an exemplary solid support 150 is illustrated with a somewhat cylindrical configuration with hemispherical ends. While the supports may have any suitable configuration, this configuration was selected as being easier to move through the carriers without the likelihood of hang up. It also provides more support area than a spherical support.

Figure 11A:
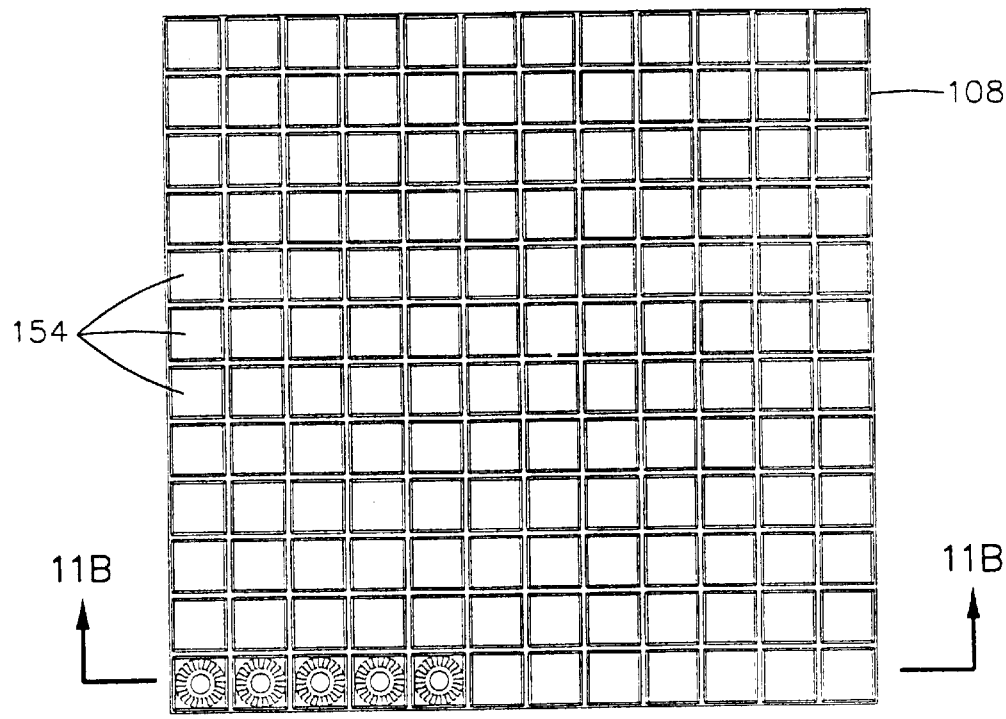
FIG. 11A is an exemplary embodiment of a carrier for a plurality of solid supports for use in the system of FIG. 2.
Figure 11B:
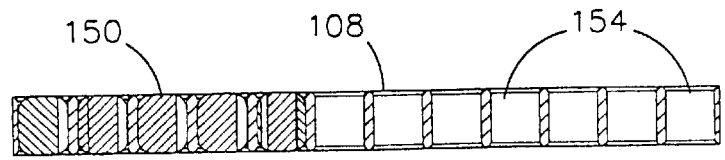
FIG. 11B is side elevation sectional view taken on line 11B—11B of FIG. 11A.

Referring to FIG. 11A, a exemplary solid support carrier 152 is illustrated with a square configuration and a twelve by twelve array of holding positions in the form of through openings 154. These holding positions or openings are preferably formed with straight sides but may have slightly converging diverging walls so that solid supports are frictionally gripped at or by the center of the opening, but are allowed to pass through with a little force. FIG. 13B illustrates a sectional view on lines 13B of FIG. 11A showing details of construction of the carrier and support.

Figure 12A:
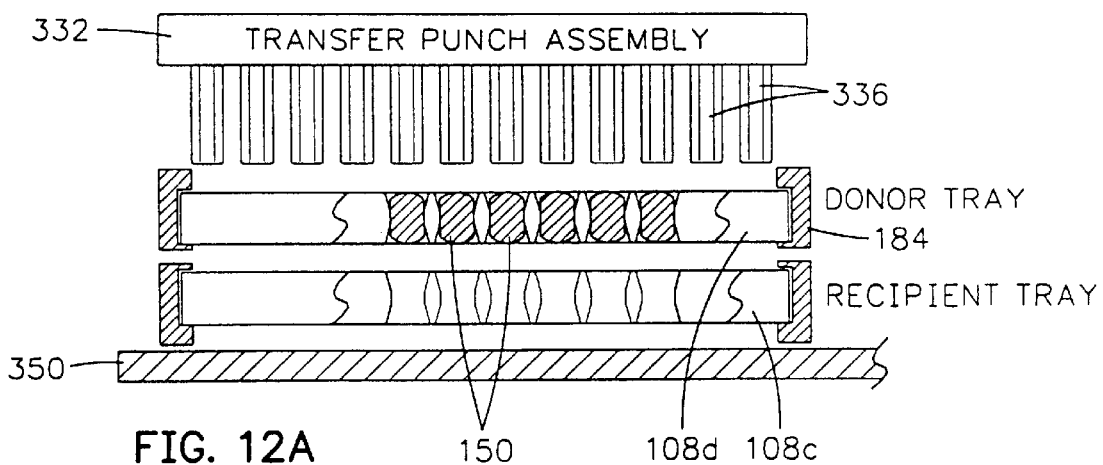
FIGS. 12A B & C are enlarged side elevation sectional views of the carrier to carrier transfer head of the apparatus of FIG. 8A carrying out the process of transfer.
Figure 12B:
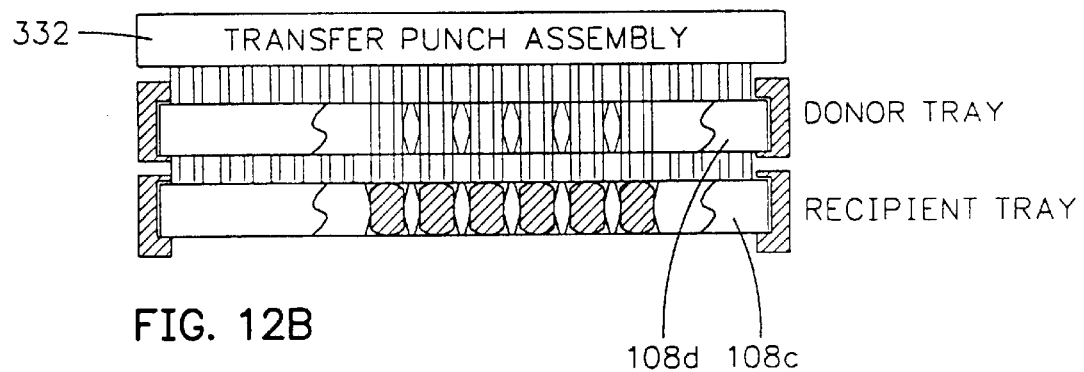
Figure 12C:
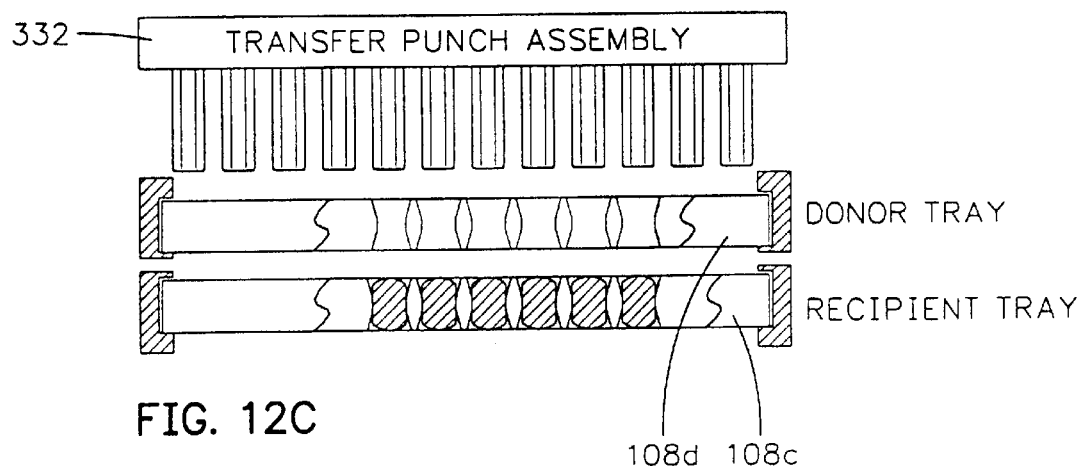

Referring to FIGS. 12A–12C, a detailed illustration of a pair of support carriers 108c and 108d and the transfer mechanism transferring supports from a donor carrier to a target carrier is illustrated. As illustrated a plurality of supports 150 are shown with a somewhat cylindrical configuration with hemispherical ends. The carriers, as previously described are configured with a grid like construction with walls forming a plurality of through openings with walls to grip and holds the solid supports in position. As shown in 14A, a loaded carrier 108d is supported in a track 182 above an empty lower carrier 108c. A transfer punch mechanism 332 is disposed above the carriers with a row of punch pins 336 aligned with a row or column of the supports in the upper carrier 108d.

The punch is activated as shown in FIG. 14B whereby the plurality of punch pins move downward and engage and move or transfer the plurality of supports from the upper carrier to the lower carrier. The punch is then retracted as shown in FIG. 14C leaving the row or column of solid supports in the lower carrier.

Figure 13:
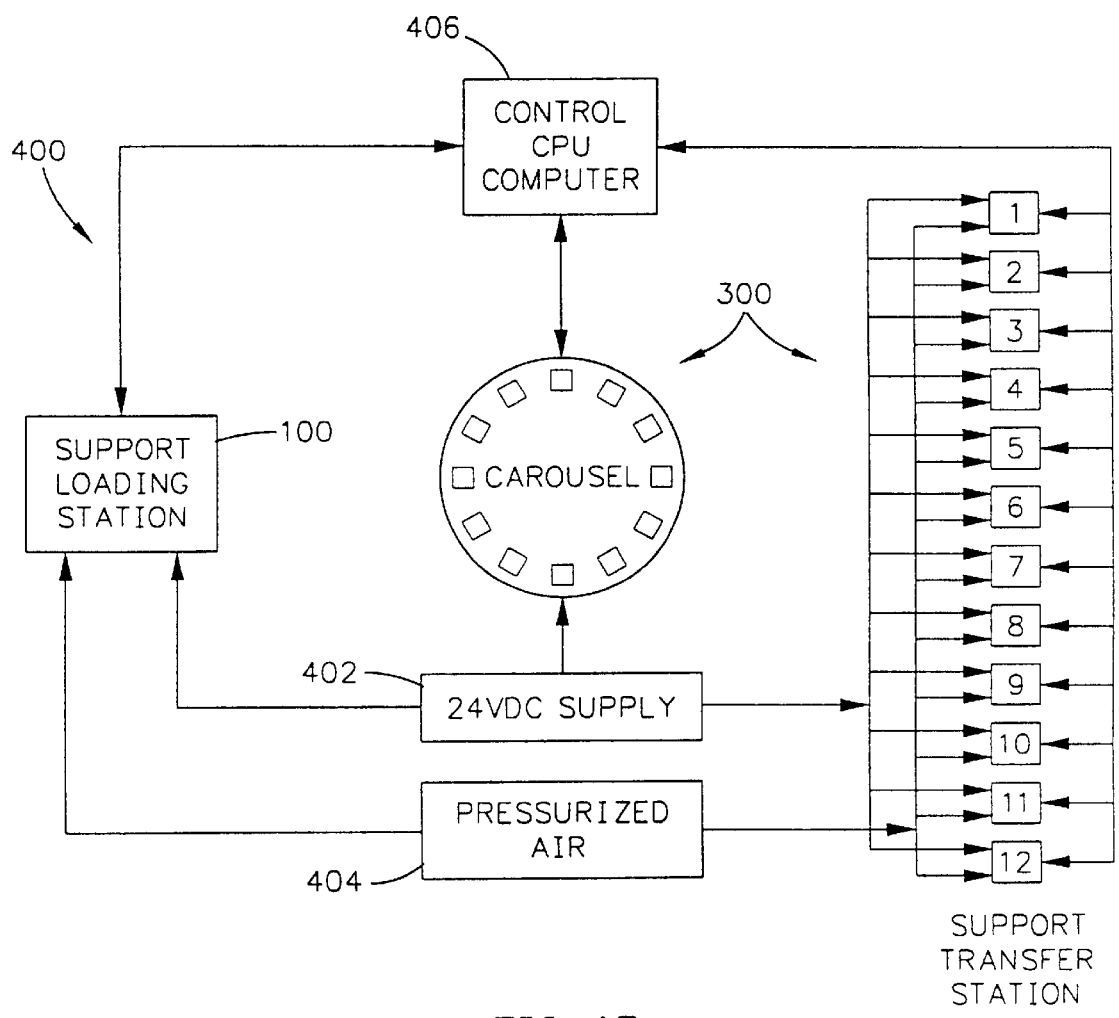
FIG. 13 a schematic illustration of a control diagram for the system of FIG. 2.

Referring to FIG. 13, a schematic illustration of an exemplery control and power system for the present system is illustrated and designated generally by the numeral 400. A low voltage D.C. power supply 402 provides power to the three main components of the system to power the various motors, valves and other components. A source of pressurized air 404 supplies air to the support loading station and to power the support transfer stations. This pressurized air powers the pneumatic motors or cylinders that power or operate the various punches, shuttles and other components of these systems. A control computer or CPU 404 is programmed to control the various valves, switches and other components and functions of the system.

Figure 14:
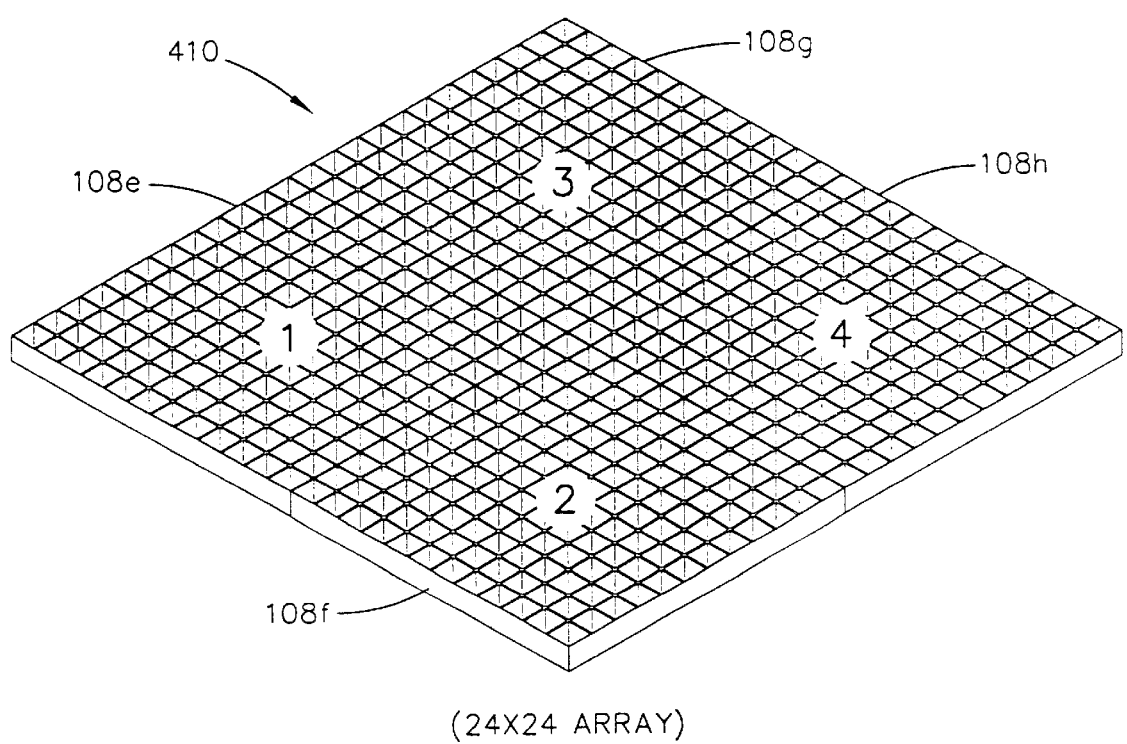
FIG. 14 is a perspective view of an exemplary embodiment of a 24×24 solid support array using four 12×12 solid support carriers for use in the system of FIG. 2

Referring to FIG. 14, a carrier arrangement of four 12×12 carriers 108e, 108f, 108g and 108h for providing a 24×24 solid support array for the present system is illustrated and designated generally by the numeral 410. Thus, a carrier or an array can consist of one or a multiple individual carriers. In addition, it will be appreciated that where multiple carriers make up an array, the individual carriers, when unloaded, become second or donee carriers. In the illustrated example, the donee carriers need be only be one fourth in number of the loaded carriers. The present invention, as described above, is preferably carried out with symmetrical arrays. However, it will be appreciated that it can be carried out utilizing unsymmetrical arrays.

As will become clear to those skilled in the art, the techniques described here can be extended to synthesize combinatorial libraries in which more than three combinatorial steps are employed and different number of monomers are applied in each chemical transformation step. In such cases it may be difficult to visualize and describe the sequence of positional transformations of solid supports among the series of arrays. A computer algorithm can be designed which takes as input the goals of a synthetic experiment: namely, the desired number of combinatorial steps and the desired number of monomers used in each combinatorial step. The algorithm can then generate a map of the protocol required to satisfy the experimental goal. This map would contain the same information as that given in the figures used herein. In the event that the experimental goal can not be satisfied the algorithm would suggest a protocol which would achieve a result as close as possible to the desired result.

The algorithm could be constructed to generate only those protocols that are consistent with a set of constraints imposed by an actual laboratory apparatus, for example, a fixed number of reaction vessels, carrier racks of a given dimension, and so forth. Such a computer algorithm would be useful for the practical application of the techniques disclosed herein. As a refinement of this method, such a computer algorithm could be designed to generate machine instructions for an automated synthetic apparatus which would perform the necessary chemical steps and positional transformations required to synthesize the desired combinatorial library.

The methods described in the body of the invention may be used to produce non-peptide, low molecular weight organic compound libraries. The synthetic chemistry protocols are more complex in the syntheses of many of these compounds than those utilized to construct peptide libraries. Additionally, there are no general methods available to directly sequence the structure of most of these compounds. Thus, the ease by which a library is decoded using the method described herein renders it suitable for the synthesis of low molecular weight compounds. The synthesis of a heterocyclic library can be demonstrated.

While we have illustrated and described our invention by means of specific embodiments, it will be appreciated that numerous changes and modifications can be made therein without departing from the spirit and scope of the invention as defined in the appended claims.

We claim:

1. A method for synthesizing, from selected monomers, a library of oligomers of defined compositions, said method comprising:

defining a number of oligomers to be synthesized and the corresponding monomers to be used;

providing a number of solid synthesis supports equal to the number of oligomers to be synthesized;

providing a first plurality of carriers for the solid synthesis supports, in which each such carrier is provided with an array of distinct holding positions for solid synthesis supports, and in which each such array includes at least three groups of distinct holding positions;

placing the solid synthesis supports in the distinct holding positions of said first plurality of carriers;

contacting each array in the first plurality of carriers with a separately defined monomer to yield an array of chemically transformed solid synthesis supports in each of said first plurality of carriers;

providing a second plurality of carriers for the solid synthesis supports, in which each such carrier is provided with an array of distinct holding positions for solid synthesis supports, and in which such array includes at least three groups of distinct holding positions for receiving said chemically transformed solid synthesis supports contained in said first plurality of carriers;

redistributing each said solid synthesis supports from each of said first plurality of carriers to a selected position in one of said second plurality of carriers; and repeating the steps of contacting and redistributing until the desired number of oligomers have been made on the solid synthesis supports, in which the position of each solid synthesis support in the arrays of distinct holding positions in each such carrier identifies the composition of the oligomer made on it.

2. A method according to claim 1 in which each array of distinct holding positions for solid synthesis supports comprises columns and rows, and in which each said group comprises a column or a row.

3. A method according to claim 2 in which each array comprises at least three columns and at least three rows.

4. A method according to claim 3 in which a step of such redistributing comprises transferring each column of solid synthesis supports from one of said first plurality of carriers to a column of solid synthesis supports in one of said second plurality of carriers.

5. A method according to claim 3 in which a step of such redistributing comprises transferring each row of solid synthesis supports from one of said first plurality of carriers to a row of solid synthesis supports in one of said second plurality of support carriers.

6. A method according to claim 2 in which:

at least one step of such redistributing comprises transferring each column of solid synthesis supports from one of said first plurality of carriers to a column of solid synthesis supports in one of said second plurality of carriers; and at least one step of such redistributing comprises transferring each row of solid synthesis supports from one of said first plurality of carriers to a row of solid synthesis supports in one of said second plurality of carriers.

7. A method according to claim 6 in which said arrays comprise at least three columns and at least three rows.

8. A method according to claim 2 in which:

all but one of said steps of redistributing comprise transferring selected columns and rows of solid synthesis supports from said first plurality of carriers respectively to columns and rows of said second plurality of carriers; and said one of said steps comprises transferring solid synthesis supports either (a) from selected columns of said first plurality of carriers to rows of said second plurality of carriers; or (b) from selected rows of said first plurality of carriers to columns of said second plurality of carriers.

9. A method according to claim 8 in which each step of contacting one of said first plurality of carriers with a monomer comprises placing such carrier in a separate reactor.

10. A method according to claim 1 in which each step of contacting one of said first plurality of carriers with a monomer comprises placing such carrier in a separate reactor.

* * * * *